(12) United States Patent
Loomis

(10) Patent No.: US 11,980,564 B2
(45) Date of Patent: May 14, 2024

(54) BACK MOBILIZER

(71) Applicant: Jaime Loomis, Naperville, IL (US)

(72) Inventor: Jaime Loomis, Naperville, IL (US)

( * ) Notice: Subject to any disclaimer, the term of this patent is extended or adjusted under 35 U.S.C. 154(b) by 126 days.

(21) Appl. No.: 17/560,714

(22) Filed: Dec. 23, 2021

(65) Prior Publication Data

US 2023/0079315 A1 Mar. 16, 2023

Related U.S. Application Data

(60) Provisional application No. 63/243,188, filed on Sep. 12, 2021.

(51) Int. Cl.
*A61F 5/02* (2006.01)
*A61F 5/01* (2006.01)

(52) U.S. Cl.
CPC .............. *A61F 5/028* (2013.01); *A61F 5/024* (2013.01); *A61F 5/026* (2013.01); *A61F 2005/0167* (2013.01)

(58) Field of Classification Search
CPC .......... A61F 5/024; A61F 5/026; A61F 5/028; A61F 2005/0167; A61F 5/03; A61F 5/02; A61F 5/01; A61F 5/022; A61F 5/37; A45F 3/04; A45F 3/047; A45F 3/06; A45F 3/14; A45F 2003/142–148; A45F 3/042; A45F 3/08; A45F 3/10; A45F 2003/045
USPC ............................................... 602/19
See application file for complete search history.

(56) References Cited

U.S. PATENT DOCUMENTS

| | | | | |
|---|---|---|---|---|
| 9,572,705 | B2* | 2/2017 | Ingimundarson | A61F 5/026 |
| 2004/0055076 | A1* | 3/2004 | Yoo | A61H 39/04 2/338 |
| 2004/0128734 | A1* | 7/2004 | Jordan | A41D 13/0007 2/69 |
| 2012/0245501 | A1* | 9/2012 | Rossi | A61F 5/026 602/19 |
| 2019/0191855 | A1* | 6/2019 | Hong | A45F 3/12 |
| 2020/0268543 | A1* | 8/2020 | Santaniello | A61F 5/028 |
| 2020/0268589 | A1* | 8/2020 | Hoy | A61H 39/04 |

FOREIGN PATENT DOCUMENTS

FR 2909861 A1 * 6/2008 ............. A61F 5/024

OTHER PUBLICATIONS

Translation of FR-2909861-A1 (Year: 2008).*

* cited by examiner

*Primary Examiner* — Keri J Nelson
*Assistant Examiner* — Seth R. Brown
(74) *Attorney, Agent, or Firm* — The Law Offices of Konrad Sherinian, LLC; Depeng Bi

(57) ABSTRACT

A therapeutic back mobilizer harness that transmits a user-applied PA force to one or both sides of the spinous process at a specific spinal segment, to improve alignment and decrease pain. The harness includes a contact member, a belt that retains the contact member, and a pull system connected to the belt. A user pulls forward on handles of the pull system to apply the PA force.

3 Claims, 6 Drawing Sheets

BACK MOBILIZER

CROSS-REFERENCE

This application claims the benefit of U.S. provisional patent application No. 63/243,188, filed Sep. 12, 2021, which is incorporated by reference herein in its entirety for all purposes.

FIELD OF THE DISCLOSURE

The present disclosure relates to back mobilizers used to isolate a specific spinal segment and mobilize that segment as the user actively moves into spinal extension in standing or in prone or as the user lies over the mobilizer in supine.

DESCRIPTION OF THE RELATED ART

Other belts related to low back pain are adapted to be used as a passive support structure. A need exists for a back mobilizer helps to actively move the spine as done in physical therapy clinics but without the need for a second person to assist in the mobilization.

SUMMARY

According to an aspect of the disclosure, a back mobilizer harness comprises a contact member; a contact member holder; and a pull system. The contact member has a posterior side and an anterior side, the anterior side of the contact member comprising at least one protrusion. The contact member holder is adapted to retain the contact member so that the at least one protrusion contacts at least one area of the user's body on at least one side of the spinous process. In embodiments, the contact member holder is a belt adapted to be worn around a user's body, or more particularly around a user's waist. The pull system is connected to the contact member holder and being adapted and configured to receive a PA force applied by the user and, when the contact member is so retained by the contact member holder, to transmit the PA force through the contact member to the at least one area of the user's body.

According to another aspect of the disclosure, a method of using a back mobilizer harness comprising the elements of the foregoing aspect comprises causing the contact member to be retained by the contact member holder, positioning the contact member holder so that the at least one protrusion of the contact member contacts the at least one area of the user's body, adjusting the pull system so that the pull system is in slight tension, so as to apply a slight PA force through the contact member to the at least one area of the user's body when the user holds the pull system in the user's hands and the user's elbows are held at a 90-degree angle at the user's sides; and the user pulling forward on the pull system to apply a PA force larger than the slight PA force through the contact member to the at least one area of the user's body.

According to another aspect of the disclosure, a method of using a back mobilizer contact member is provided. The back mobilizer contact member has a posterior side and an anterior side, the posterior side of the contact member being adapted to support the contact member on a horizontal support surface with the anterior side facing upwardly, the anterior side of the contact member comprising at least one protrusion, the at least one protrusion being adapted to contact at least one area of the user's body on at least one side of the spinous process. The method comprises placing the contact member directly on the horizontal support surface, and a user lying over the contact member with the at least one protrusion contacting the at least one area of the user's body, the user's body weight causing a PA force to be transmitted through the at least one protrusion to the at least one area of the user's body.

BRIEF DESCRIPTION OF THE DRAWINGS

Although the characteristic features of this disclosure will be particularly pointed out in the claims, the subject matter of the claims, and the manner in which it may be made and used, may be better understood by referring to the following description taken in connection with the accompanying drawings forming a part hereof, wherein like reference numerals refer to like parts throughout the several views and in which:

DETAILED DESCRIPTION

Figure 1:
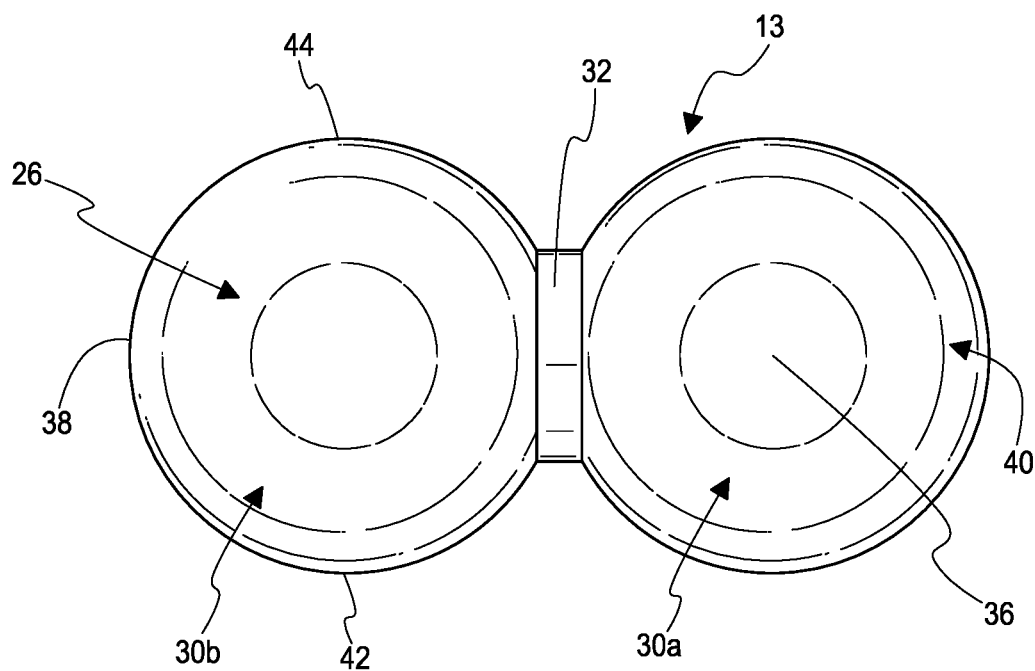
FIG. 1 is an anterior view of a back mobilizing contact member according to an embodiment.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, unless otherwise clearly stated, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting unless the claims expressly state otherwise.

Back mobilizer harnesses according to embodiments of the disclosure are adapted and configured to isolate a specific segment of the spine and mobilize the spine using a posterior-anterior (PA) force. This PA force helps to realign the spine, decrease pain and muscle spasm as typically used with manual application in Physical Therapy. With improved spinal alignment the harness will also help to improve muscle output and physical performance. When used as directed, pursuant to a method of use according to an embodiment of the disclosure, it is believed that the back mobilizer harness will also decrease recurrence of back and prevalence of sciatic type nerve pain. The back mobilizer harnesses generally comprise a contact member, a contact member holder adapted to retain the contact member, and a pull system connected to the contact member holder, the pull system being adapted to transmit a PA force applied by a user through the contact member and to one or both sides of a symptomatic area of a user's spine. The contact member holder of the illustrated embodiment is a belt that is adapted to be worn by a user, the belt being fastened around the user's body at the level of the symptomatic area of the user's spine. In other embodiments, the contact member holder is not worn by the user between applications of PA force, but rather positioned as desired prior to each force application, such as by the user holding and moving the harness by the pull system to position the contact member over the symptomatic area, in a method of use of the harness according to an embodiment. Such a method of use Now described is a back mobilizer harness 10 according to an embodiment of the disclosure, as illustrated in FIGS. 1-12. The back mobilizer harness 10 includes a durable elastic supportive harness belt 12, a contact member 13, and a pull system 15. The contact member 13 is removably retained by the harness belt 12 so as to transmit the PA force to a user's back when a user is wearing the harness 10, the PA force being supplied by the user pulling on the pull system 15.

The harness belt 12 is adapted to be worn around a user at a spinal level that is symptomatic. The harness belt 12 may, for example, be formed of neoprene (a/k/a polychloroprene) or similar material. The harness belt 12 has a belt first end 14, a belt second end 16, a belt upper edge 17, a belt lower edge 19, a belt anterior side 21, and a belt posterior side 23. The belt upper edge 17 and the belt lower edge 19 are generally parallel, and the belt anterior and belt posterior sides 21, 23 generally extend from the belt upper edge 17 to the belt lower edge 19 and from the belt first end 14 to the belt second end 16. The harness belt 12 has a belt length and a belt width, the belt length extending generally from the belt first end 14 to the belt second end 16 along a longitudinal belt axis, and the belt width extending across the harness belt 12 generally perpendicularly to the belt axis. More particularly, the harness belt 12 is adapted to be worn so as to extend longitudinally around a user approximately at a level of the user's waist. The harness belt 12 harness belt 12 comprises first and second mutually complementary hook-and-loop fastener patches 18 and 20, the first hook-and-loop fastener patch 18 being disposed at the first end 14 and the second hook-and-loop fastener patch 20 at the second end 16. Thus, the harness belt 12 can be secured at a desired tightness around the user when the patches 18 and 20 are pressed together at a relative tightness position selected for the user's comfort. The harness belt 12 can be made in various sizes to fit a variety of users. In an embodiment, the harness belt 12 has a 4-inch belt width and a 43-inch belt length. The harness belt 12 comprises a pocket 22 for receiving a contact member 13 on the anterior side 21 of the harness belt 12. When the harness 10 is assembled and worn according to an embodiment of a method of use, the contact member 13 straddles the spinous process (the most prominent part of the spine) to its left and right sides (see FIGS. 1-4). This is meant to isolate a specific spinal segment anywhere from the sacral spine to the cervical spine, which can be adjusted by the user adjusting the height (i.e., the position along the length of the user's spine) at which the harness belt 12 is fastened around the user.

Figure 2:
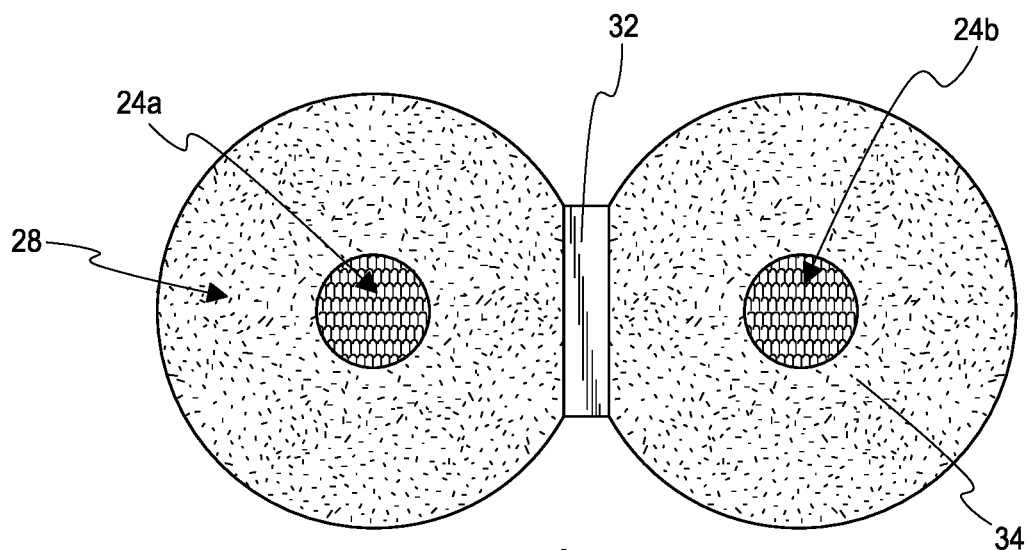
FIG. 2 is a posterior view of the contact member of FIG. 1.

The illustrated back mobilizer harness 10 uses a contact member 13, depicted separately in FIGS. 1 and 2. The contact member 13 is formed of a suitable material, such as 100% rubber, and has the shape and mechanical properties of one half of a common massage "peanut" cut along a frontal plane of symmetry. Thus, the contact member 13 has a contoured contact member anterior side 26 and a generally flat contact member posterior side 28. The contact member anterior side 26 comprises a first protrusion 30a, a second protrusion 30b, and a connecting segment 32, the first and second protrusions 30a, 30b being connected by the connecting segment 32. In other embodiments, contact members for use in a back mobilizer harness according to this disclosure are formed of different materials with different densities, and in various shapes and sizes. Materials, shapes, and sizes of a contact member according to the disclosure may be adapted to a user's specific size, comfort, and desired outcomes and/or for efficient manufacturing or other considerations.

In another embodiment (not shown), a complementary pair of contact members may be used in place of a single half-peanut-shaped contact member, the pair of contact members being shaped as though formed by cutting the half-peanut shaped contact member 13 in half through its connecting segment 32 to form two "single protrusion" contact members, each single protrusion contact member comprising one of the protrusions 30a, 30b. Each such single protrusion contact member would thus be generally formed as a 2.5-inch diameter hemisphere, thus having a 1.25-inch depth In embodiments of methods according to the disclosure, a massage harness retaining only one such single protrusion contact member may be used to isolate the left or the right side of the spine, or both contact members may be retained at once to apply a PA force to both sides of the spine. In an embodiment, the PA forces thus applied are equal, thus obtaining a similar result to the contact member 13. In other embodiments, two single protrusion contact members retained at once differ in their materials and/or construction, so that different PA forces are applied to the different sides of the spine.

In other embodiments, contact members having variously shaped contoured sides are used in a back mobilizer harness according to the disclosure. For example, instead of having hemispherical protrusions adapted to contact each side of the spinous process, a contact member may have generally conical, frustoconical, or pyramidal protrusions. In other embodiments, instead of having protrusions generally tapering to a point or inner concentric area, a contact member has protrusions of elongate shapes, such as hemispherical or prismatic shapes, that are adapted to align generally parallel to the spine on each side. In addition, the shapes of the protrusions need not be symmetrical to the right and left of their contact regions, but rather may have "wedge" shapes.

Suitable materials for a contact member according to embodiments may have one or more desired properties such as a desired density, compressibility, flexibility, durability, and/or other material property or performance characteristic. Examples of suitable contact member materials include natural rubber, expanded polypropylene (EPP) closed-cell foam, ethylene vinyl acetate (EVA) closed-cell foam, and combinations thereof.

In other embodiments, as an alternative to a solid or closed-cell foam contact member, such as the contact member 13, an inflatable contact member (not shown) may be used to apply pressure to either side of the spinous process. Such an inflatable contact member may be adapted to be inflated or deflated to vary the amount of pressure applied. The pressure can be based on a specific user's needs, symptoms pertaining to low back pain and alignment, and/or personal preferences, any of which may vary from use to use.

The contact member 13 has a depth, a length, and a width described here with reference to the orientation of the contact member relative to the body of a user using the contact member according to embodiments of the disclosure. The depth extends in the aforementioned PA direction from a contact member posterior end 34 (which in the illustrated embodiment is a point on the contact member posterior side 28) to a contact member anterior end 36, the length is measured in a mediolateral (ML) direction from a contact member right end 38 to a contact member left end 40, and the width extends in a vertical or craniocaudal (CC) direction (generally parallel to the spine) from a contact member lower end 42 to a contact member upper end 44. Without limitation, the depth (as illustrated, approximately a radius of one of the hemispherical protrusions 30a, 30b) may, for example, be from about 0.5 inch to about 2.5 inches, or more preferably about 1.25 inch; the length (illustrated as approximately two protrusion diameters) may be from about 2 inches to about 10 inches, or more preferably about 5 inches; and the width (illustrated as approximately the diameter of one of the protrusions) may be from about 1 inch to about 5 inches, or more preferably about 2.5 inches. The contact member anterior end 36 comprises at least a portion of at least one the protrusions 30a, 30b, such as an apex/vertex (a point), ridge (a generally one-dimensional line or curve), or plateau (a two-dimensional area) thereof. The connecting segment 32 is shallower than the protrusions 30a, 30b, thus providing a posterior clearance between the anterior end 36 and the connecting segment 32, for allowing the spinous process (the bony prominence) to extend rearwardly beyond the anterior end 36 of the contact member 13.

Figure 3:
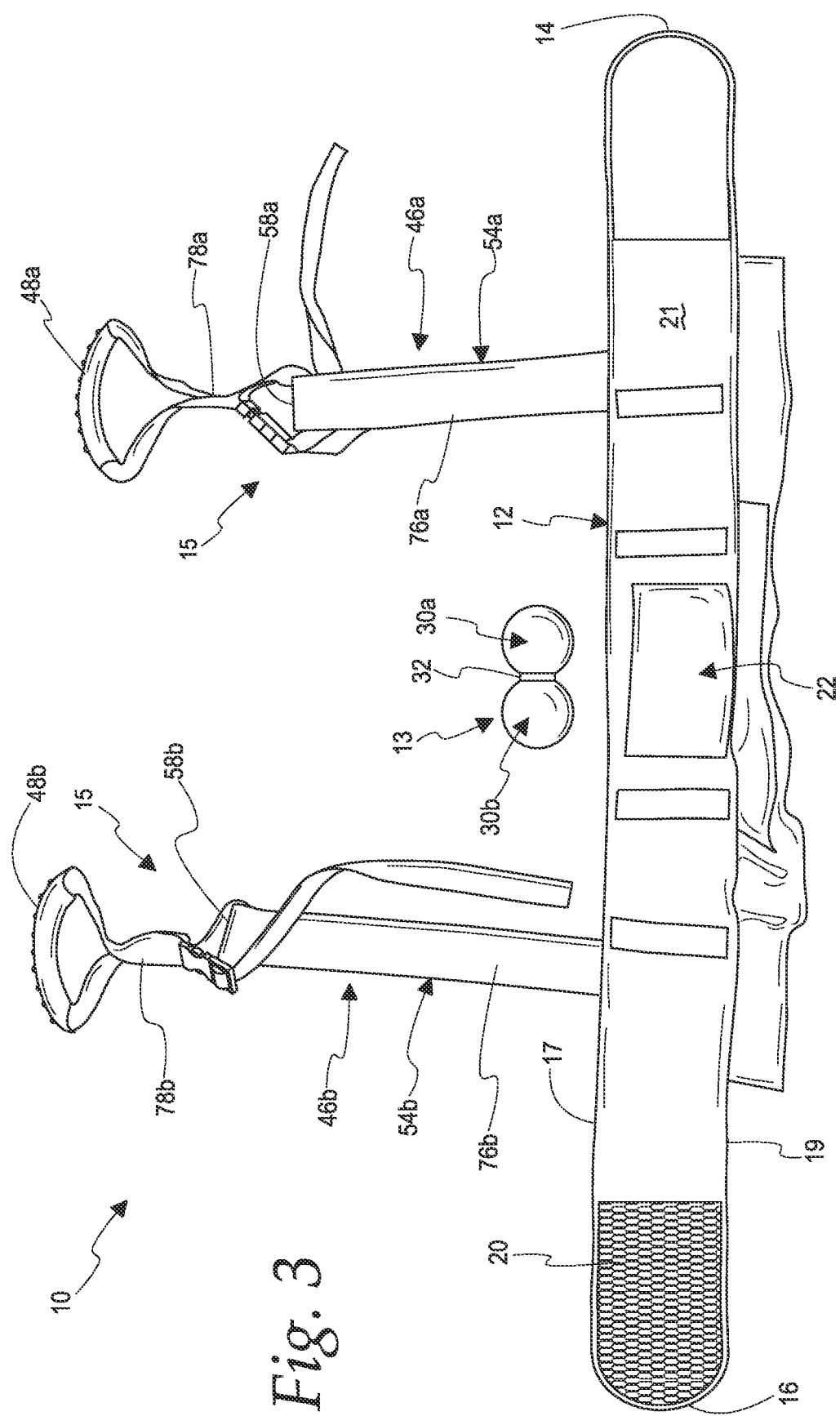
FIG. 3 is an exploded anterior view of a back mobilizer harness according to an embodiment.
Figure 4:
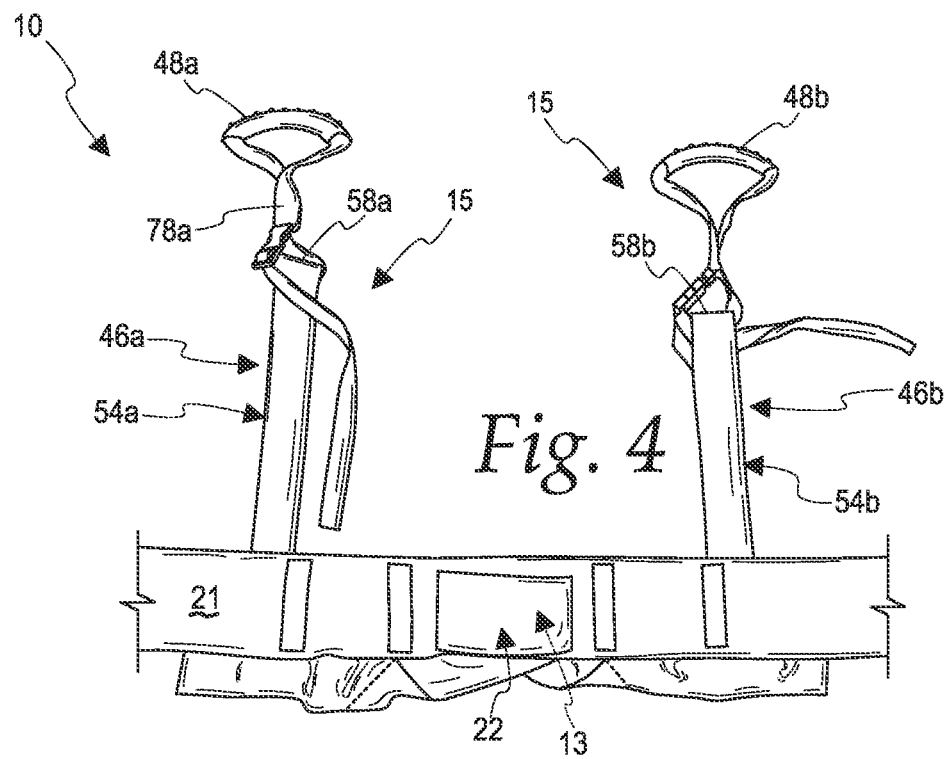
FIG. 4 is an anterior view of the back mobilizer harness of FIG. 3.

The contoured, anterior side 26 of the contact member 13, best seen in FIG. 1 is adapted to face the body of a user U and lie over opposite lateral sides of the spinous process of the lumbar spine. A user can adjust the vertical (CC) position where the contact member 13 lies across the spine by adjusting the height at which the harness belt 12 is fastened. Shown in FIG. 2 is the flat, posterior side 28 of the contact member 13, which is adapted to face away from the posterior side of a user's body. The contact member 13 is adapted to slide into, and to attach to the inside of, the pocket 22 by hook-and-loop fastener patches 24a, 24b to decrease slipping and maintain position in the neoprene sleeve. The assembly of the back mobilizer harness 10 is illustrated in the exploded and assembled views of FIGS. 3 and 4, depicting the contact member 13 and harness belt 12 in an anterior view facing the inside of the harness belt 12 or the part of the harness belt 12 that is adapted to be in contact with a user's body. In FIG. 3, the contact member 13 is being shown above the belt in the position it will slide into the sleeve, while the contact member 13 has been placed inside of the sleeve in the assembled configuration of the back mobilizer harness 10 as shown in FIG. 4.

Figure 7:
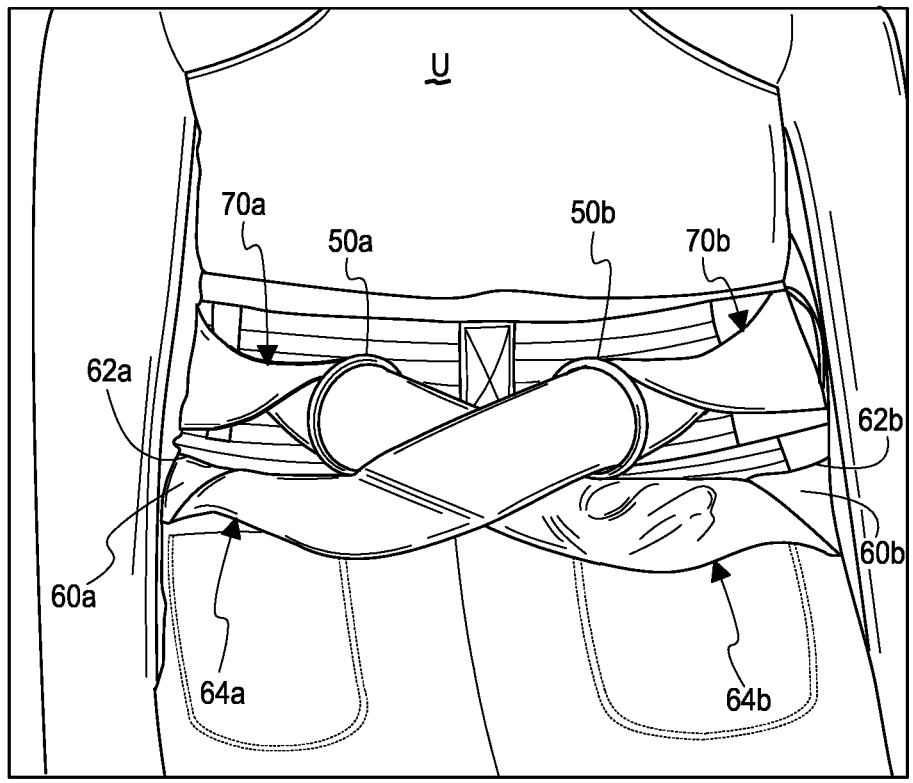
FIG. 7 is a posterior view of the harness of FIG. 3 as worn by a standing user.
Figure 8:
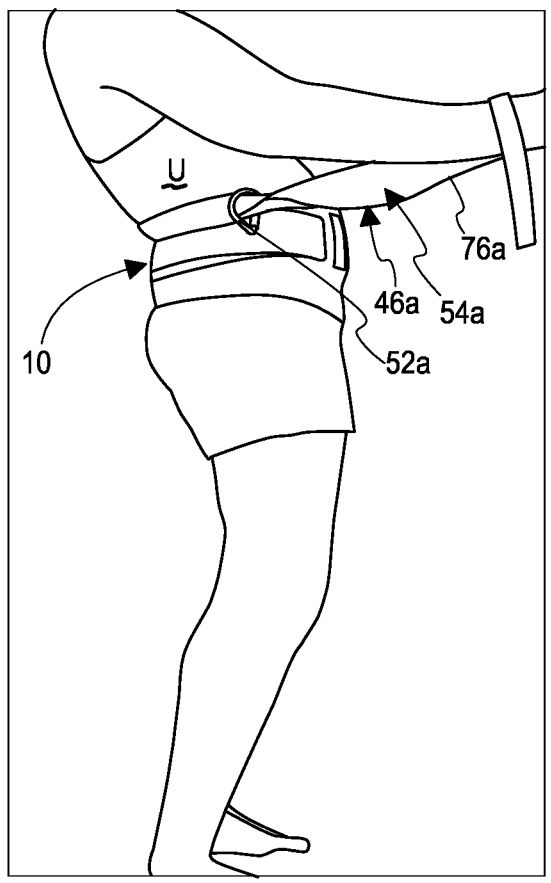
FIG. 8 is a right-side view of the harness of FIG. 3 as worn and used by a standing user in a method according to an embodiment.

With reference to FIGS. 5 and 7-11, the pull system 15 of the harness 10 is now described. The pull system 15 includes an elongate left strap 46a, a left handle 48a connected to the left strap 46a, first and second left strap guides 50a, 52a through which the left strap 46a is threaded, an elongate right strap 46b, a right handle 48b connected to the right strap 46b, and first and second right strap guides 50b, 52b through which the right strap 46b is threaded. The left strap 46a has a left strap free length 54a extending from a proximal left strap fixed end 56a to a distal left strap free end 58a. In the illustrated embodiment, the left strap fixed end 56a is comprised in a fixed strap segment 60a of the left strap 46a that is stitched to the harness belt 12 by a first left strap stitch seam 62a, the first left strap stitch seam 62a affixing a portion of a longitudinal side of the left strap 46a to a portion of the belt lower edge 19. Likewise, right strap 46b has a right strap free length 54b extending from a proximal right strap fixed end 56b to a distal right strap free end 58b. In the illustrated embodiment, the right strap fixed end 56b is comprised in a fixed strap segment 60b of the right strap 46b that is stitched to the harness belt 12 by a first right strap stitch seam 62b, the first right strap stitch seam 62b affixing a portion of a longitudinal side of the right strap 46b to a portion of the belt lower edge 19. As illustrated in FIGS. 7 and 8, the left and right straps 46a, 46b are respectively attached to a portion of the belt lower edge 19 that is adapted to wrap around the opposite hip of a user wearing the harness belt 12, so that the first left strap stitch seam 62a generally extends around the user's right hip and the first right strap stitch seam 62b generally extends around the user's left hip when the harness belt 12 is worn. Each strap 46a, 46b further comprises folds and additional stitching as described below.

Figure 5:
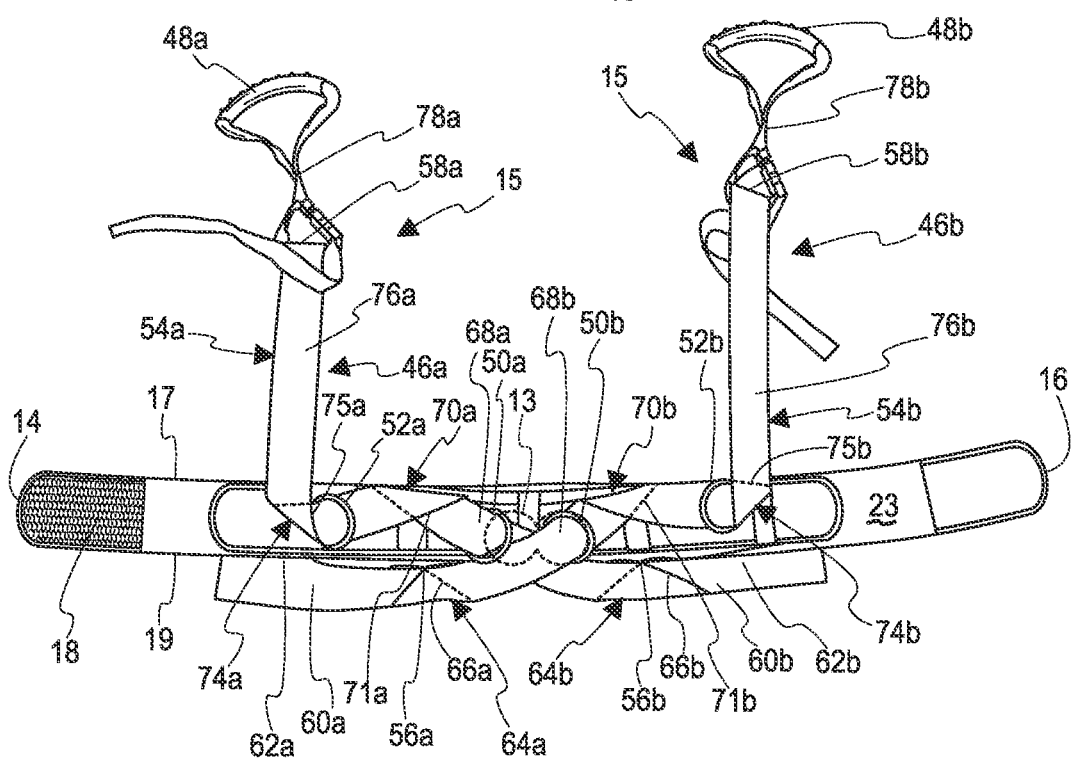
FIG. 5 is a posterior view of the back mobilizer harness of FIG. 3.

As shown in the posterior view of FIG. 5, the straps 46a, 46b are sewn to themselves at upwardly inclined angles at a first left strap fold 64a and a first right strap fold 64b by a second left strap stitch seam 66a and second right strap stitch seam 66b, respectively, at the respective left and right strap fixed ends 56a, 56b. Thus, the left and right strap free lengths 54a, 54b, comprise respective first free strap segments 68a, 68b, which, in a relaxed state, extend distally from the first folds 64a, 64b at the upwardly inclined angles, so as to cross and form an "X" overlapping the contact member 13 when the contact member 13 is retained by the harness belt 12, the first folds 64a, 64b tending to resist such straightening of the respective straps 46a, 46b as would reduce the inclination angles of the first free strap segments 68a, 68b which form the "X". A substantial portion of the flat, posterior side 28 of the contact member 13 is overlapped by at least one of the first free strap segments 68a, 68b, as illustrated by the dashed outline of the contact member 13 shown in FIG. 5. Thus, when a user pulls the handles 48a, 48b, the straps 46a, 46b apply PA pressure to the contact member 13, the PA pressure being distributed over a substantial area of the posterior side 28 of the contact member 13. The angled pull system 15 thus allows for the mobilization of the spine using the contact member 13 as the direct pressure point. In addition, it is believed that two straps wrapping around a posterior side of a contact member in two different directions tends to beneficially resist tipping or sliding movement of the contact member in any direction, thus stabilizing the points of contact on the user's back.

The first free strap segments 68*a*, 68*b* are free to glide through the respective first guides 50*a*, 50*b* as the user actively pulls on the straps 46*a*, 46*b* with the handles 48*a*, 48*b*. The guides 50*a*, 50*b*, are depicted as metal rings attached to the belt 12, such as being hemmed into a connecting piece of material similar to that of the straps 46*a*, 46*b*, but may alternatively be other rigid or flexible forms through which the first free strap segments 68*a*, 68*b* can be threaded, such as plastic rings or fabric loops. The first guides 50*a*, 50*b* generally retain the first free strap segments 68*a*, 68*b* in their crossed orientation between uses of the harness 10. In addition, the first guides 50*a*, 50*b* may resist straightening of the first free strap segments 68*a*, 68*b* under tension supplied by the user, such as would otherwise tend to flatten the "X," although in embodiments, transverse forces produced by internal stresses in folds sewn into the respective straps, including the first folds 64*a*, 64*b* as well as additional folds described below, serve to relieve the first and second guides 50*a-b*, 52*a-b* of at least some of the loading to resist such straightening. Benefits of the various strap folds bearing such loads as internal stresses, rather than the guides 50*a-b*, 52*-a-b* transmitting transverse forces to portions of the respective straps 46*a*, 46*b*, may include avoiding or reducing bunching and/or twisting of the straps 46*a*, 46*b*, as well as isolating the belt 12 itself from transverse forces required to "bend the load paths" through the respective straps 46*a*, 46*b*.

There are two other folds sewn into the straps 46*a*, 46*b*, as now described. The left and right straps 46*a*, 46*b* respectively comprise a second left strap fold 70*a* and second right strap fold 70*b*, affixed by respective third stitch seams 71*a*, 71*b*, each second fold 70*a*, 70*b* forming a distal end of the respective first free strap segment 68*a*, 68*b*, as well as forming a proximal end of a left second free strap segment 72*a* and a right second free strap segment 72*b*, respectively. In a relaxed state of the strap 46*a*, 46*b*, the respective second free strap segment 72*a*, 72*b* extends generally horizontally (that is, along the length of the belt 12), and the second folds 70*a*, 70*b* resist the tendency of the straps 46*a*, 46*b* to straighten under tension supplied by the user (which is typically vertically—or craniocaudally—inclined away from the user's waist and toward the user's shoulders), such as would tend to incline the second free strap segment 72*a*, 72*b* upwardly away from the horizontal longitudinal axis of the belt 12 when worn. Finally, the left and right straps 46*a*, 46*b* further include a third left strap fold 74*a* and a third right strap fold 74*b*, affixed by respective fourth stitch seams 75*a*, 75*b*, each of which is upturned so as to define a distal end of the respective second free strap segment 72*a*, 72*b*, as well as to define a proximal end of a third free left strap segment 76*a* or third free right strap segment 76*b*, respectively, the third free strap segments 76*a*, 76*b* being angled upwardly from the second free strap segments 72*a*, 72*b* when the straps 46*a*, 46*b* are in relaxed states. More particularly, while the first strap folds 64*a*, 64*b* form a upward facing obtuse first angle, and the second strap folds 70*a*, 70*b* form a downward facing obtuse second angle that is equal or approximately equal in magnitude to the first angle, the third strap folds 74*a*, 74*b* form an upturned right or approximately right third angle, such that the third free strap segment 76*a*, 76*b* deviates the most sharply of any of the strap segments from the longitudinal orientation of the proximally adjacent portion of the respective strap 46*a*, 46*b* (i.e., from that of the preceding free strap segment, or in the case of the first free strap segments 68*a*, 68*b*, from that of the respective fixed strap segment 60*a*, 60*b*).

Figure 6:
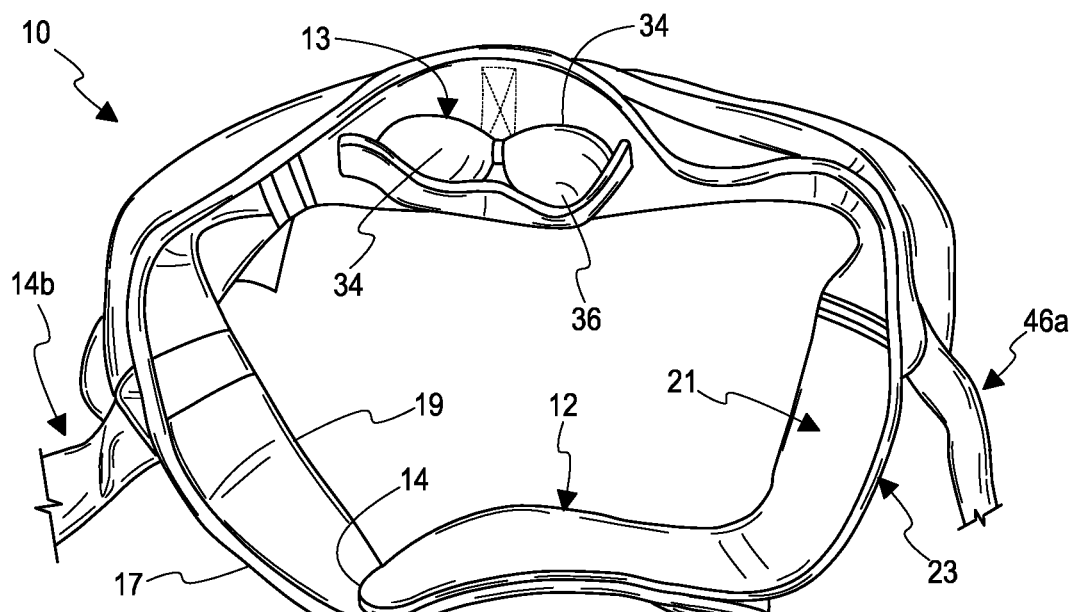
FIG. 6 is a top view of the back mobilizer harness of FIG. 3.

Shown in FIG. 6 is a superior view of the harness belt 12, disposed as though strapped around a user's waist. The harness belt 12 fastens in the front with hook-and-loop fastener patches 18, 20 over the user's belly, tightened dependent on the user's waist size. The contact member 13 is seen placed in the pocket 22 with the contact member anterior side 26 facing inwards, where it will be in contact with the user's spine. Turning to FIG. 7, a posterior view of the back mobilizer harness 10 as worn by a user is shown.

The left and right straps 46*a*, 46*b* of the pull system 15 can be either firm nylon heavy webbing straps or more stretchable elastic straps, the latter producing a more gradual increase in pressure across the spine as the user pushes the handles forward to tension the straps 46*a*, 46*b*. The left and right straps 46*a*, 46*b* have corresponding left and right easy-grip handles 48*a*, 48*b* (plastic and/or foam) attached to their respective free ends 58*a*, 58*b*. The handles 48*a*, 48*b* may be connected to the strap free ends 58*a*, 58*b* by a respective adjustable-length connecting section 78*a*, 78*b*, which can be shortened or lengthened so that a fully extended distance of the handle from the respective strap fixed end 56*a*, 56*b* when the respective free length 54*a*, 54*b* is slightly tensioned is adjusted to fit a particular user, as described further below. In other embodiments (not shown), the free lengths 54*a*, 54*b* of the straps themselves are of adjustable length, in either case providing a way to vary the distance of the handle 48*a*, 48*b* from the respective strap fixed end 56*a*, 56*b*. In FIGS. 8-11, the back mobilizer harness 10 is shown as disposed when worn and used, in methods according to embodiments described below.

In one embodiment of a method of use, the back mobilizer harness 10 is used in a standing position as illustrated in FIG. 8. To use the harness 10 in standing posture, a user fastens the harness belt 12 around the user's abdomen and tightens the hook-and-loop fastener straps to the user's comfort. The harness belt 12 should feel tight, but the user should feel free to move and breathe without discomfort. Next the user holds the handles 48*a*, 48*b* in each hand. The user adjusts the positions of the handles 48*a*, 48*b* (in the illustrated embodiment, by adjusting the lengths of the connecting sections 78*a*, 78*b*, while in other embodiments this may be done by adjusting the lengths of the straps 46*a*, 46*b* themselves, as mentioned previously) so that there is slight tension when the user's elbows are held at a 90-degree angle at the user's sides. Next, the user bends back, extending the spine as one would during a back bend, while at the same time pushing in a forward or anterior direction on the handles 48*a*, 48*b*, extending or straightening out the elbows to maintain pressure and tension across the contact member 13 retained by the harness belt 12. The user should extend as far back as the user can hold, hold for a count of two seconds at the user's end range, and return to a full upright position with the user's arms returning to the 90-degree angle at the user's sides. The user uses their arms to add as much or as little tension as is comfortable. The user repeats the foregoing steps for ten repetitions or as directed by the user's physical therapist.

Figure 9:
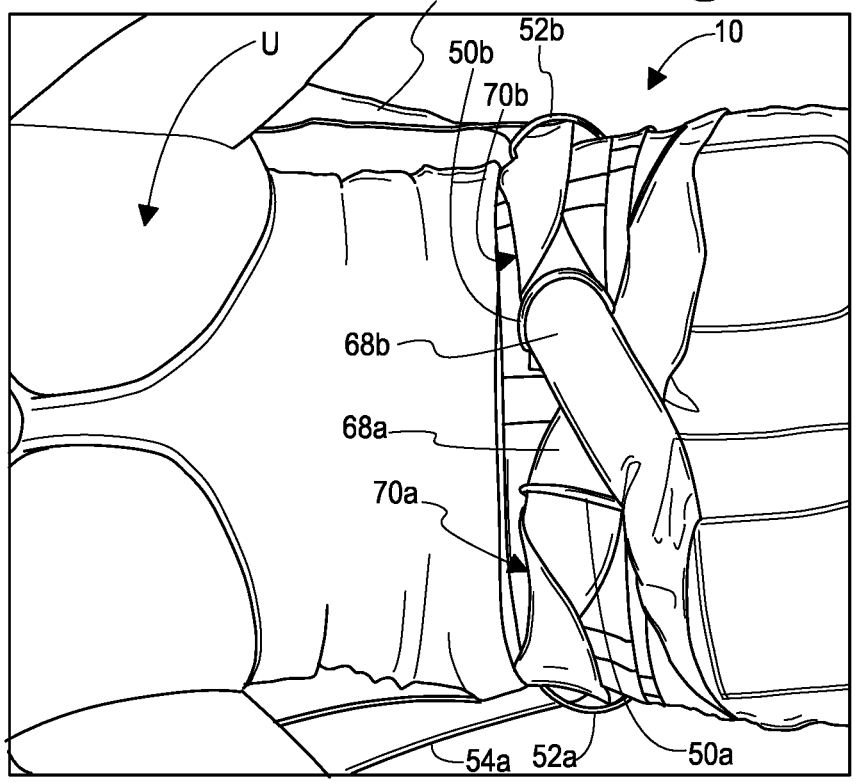
FIG. 9 is a top view of the harness of FIG. 3 as worn by a user in a prone position.
Figure 10:
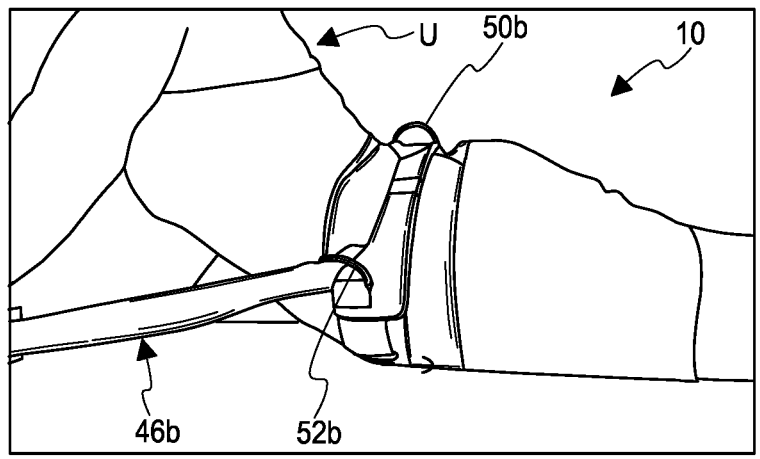
FIG. 10 is a left-side view of the harness of FIG. 3 as worn and used by a user in a prone position.
Figure 11:
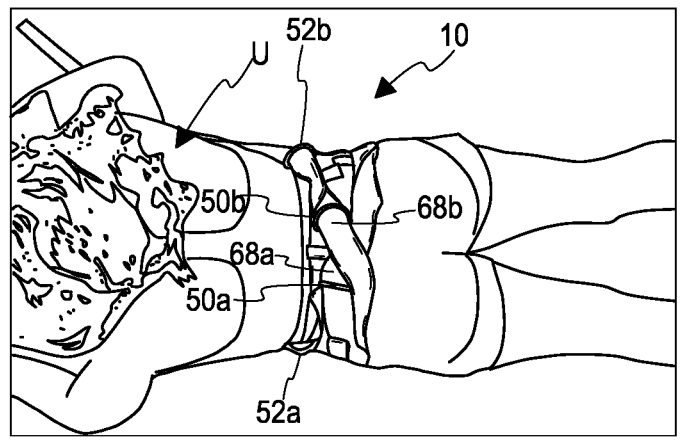
FIG. 11 is a top view of the harness worn and used by a user in a prone position as in FIG. 10.

In another embodiment of a method of use, the back mobilizer harness 10 is used in a prone position as illustrated in FIGS. 9-11. FIG. 9 is a top view of the back mobilizer harness 10 as worn by a user as they lie in a prone position. The third free strap segments 76*a*, 76*b* are angled to come up towards the arms and shoulders at about a ninety-degree angle. To use the back mobilizer harness 10 in prone, a user fastens the harness belt 12 around the user's abdomen and tightens the hook-and-loop straps to the user's comfort. The harness belt 12 should feel tight, but the user should feel free to move and breathe without discomfort. Next the user lies in the prone position or on the user's belly (the user can use a yoga mat, firm mattress or other sturdy surface for comfort) and places the user's hands, palms-down, directly underneath the user's shoulders like in push-up position. The user adjusts the positions of the handles 48a, 48b so that there is slight tension when holding them directly underneath the user's shoulders (once adjusted after the first use, the user should not have to change the handle position again; it is a one-time adjustment for personal sizing). Now the user presses up by extending elbows to lift the user's chest and upper abdomen from the ground while keeping the user's hip bones on the floor (or other chosen surface). The user keeps hands and handles 48a, 48b in the same position to allow for gradual and constant pressure across the contact member 13 placed on the user's lower/lumbar spine. The user presses as high up as the user can while maintaining hips on the ground, holds for a count of two seconds, and returns to the prone position with the user's chest resting back on the ground. The user repeats ten times or as directed by the user's physical therapist. This move is known as a prone press up or cobra pose in yoga. The harness 10 is adding an over-pressure to the movement to mobilize the most restricted or symptomatic part of the body, which is usually segments L4-L5. This is meant to simulate a prone press up with an overpressure used in physical therapy clinics to improve spinal alignment, decrease pain and improve overall functional mobility and strength. This pressure can otherwise not be created without the use of a second person applying the direct pressure as the contact member 13 and angled strap pull system 15 are designed.

Unlike static support belts or other back pain-relieving belts, the back mobilizer harness of the present disclosure requires the user to actively stretch and move while the harness increases the amplitude and efficiency of the spinal extension. The harness belt is easy to don/doff by the single user but the user may need the professional guidance of a physical therapist to ensure proper use. If used correctly, this has been shown to decrease back pain and improve muscle output, as shown by both manual muscle testing and other objective measures of strength.

Different sized harnesses can not only be used for different sized users, but they can also be used to isolate different levels of the spine including the thoracic spine and cervical spine. Harnesses for mobilizing the thoracic spine can be used the same as the lower lumbar spine in either standing or prone posture, but it can also be used in sitting posture. A harness for mobilizing the cervical spine can be used in sitting, standing or supine posture. Harnesses for mobilizing the cervical and thoracic spine may have slightly different angled straps and different sized and/or different shaped contact members; however, all harnesses will be used to isolate a specific spinal segment and to create a posterior-anterior force in order to decrease pain and improve alignment and overall mobility.

In some embodiments, the harness excludes a "belt" or analogous structure, instead wrapping only around the posterior of the user's spine and being held in place solely by the pull system during application of the PA force by the user. In other embodiments, a harness includes a contact member holder that is wearable, but which does not tighten against the anterior side of the user's body directly opposite the contact member. Such a wearable contact member holder may transmit passive holding force to another part of the anterior side of the wearer's body, such as by way of a rigid brace or collar member. More particularly, an embodiment of a harness for mobilizing the cervical spine excludes a belt that would tighten against the anterior side of a user's neck when worn.

Figure 12:
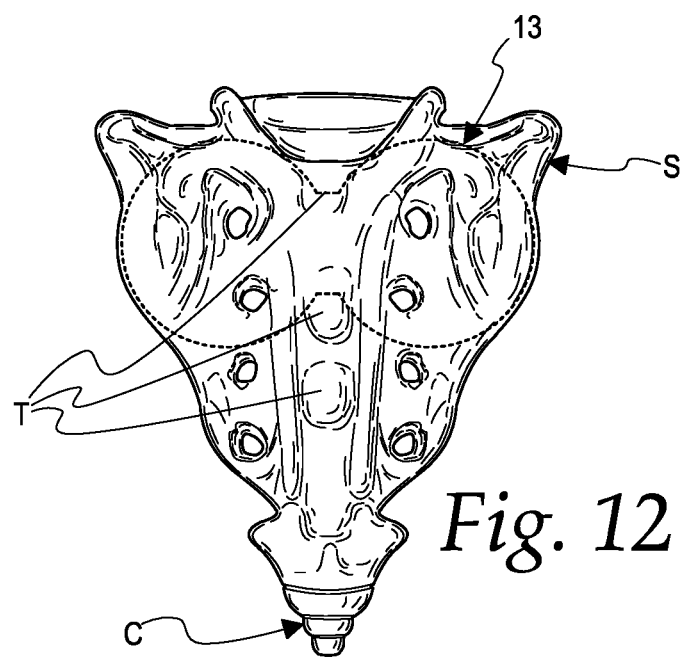
FIG. 12 is a posterior view of a contact member positioned directly over a sacrum as in a method according to another embodiment.

In a method according to another embodiment, a contact member according to this disclosure is placed directly on the floor or other horizontal support surface, and a user lies supine directly over the contact member, using their weight to apply a PA force to areas on one or both sides of the symptomatic area of the spine. This method may use the contact member 13 or another contact member that has a posterior side that is adapted to engage a firm planar support surface, such as a floor surface, and a contoured anterior side having one or more contact protrusions for contacting and transmitting the PA force to the user's body. More particularly, as illustrated in FIG. 12, in a posterior view of a contact member 13 positioned for use, relative to the sacrum S and coccyx C of a user, a user may lie supine directly over the contact member 13 in such a manner that the protrusions 30a, 30b apply a PA force to the sacrum S on each side of the spinous tubercles T. In an embodiment, this method can be used to "level" the sacrum, that is, to correct a tilt in the sacrum so that neither the left nor the right side of the sacrum is "elevated" in the posterior direction relative to the other side.

These and other advantages of the invention will be further understood and appreciated by those skilled in the art by reference to the following written specification, claims and appended drawings. Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

The foregoing description of the disclosure has been presented for purposes of illustration and description and is not intended to be exhaustive or to limit the disclosure to the precise form disclosed. The description was selected to best explain the principles of the present teachings and practical application of these principles to enable others skilled in the art to best utilize the disclosure in various embodiments and various modifications as are suited to the particular use contemplated. It should be recognized that the words "a" or "an" are intended to include both the singular and the plural. Conversely, any reference to plural elements shall, where appropriate, include the singular.

It is intended that the scope of the disclosure not be limited by the specification but be defined by the claims set forth below. In addition, although narrow claims may be presented below, it should be recognized that the scope of this invention is much broader than presented by the claim(s). It is intended that broader claims will be submitted in one or more applications that claim the benefit of priority from this application. Insofar as the description above and the accompanying drawings disclose additional subject matter that is not within the scope of the claim or claims below, the additional inventions are not dedicated to the public and the right to file one or more applications to claim such additional inventions is reserved.

The invention claimed is:

1. A back mobilizer harness comprising a contact member;

a contact member holder; and a pull system;

the contact member having a posterior side and an anterior side, the anterior side of the contact member comprising at least one protrusion;

the contact member holder being adapted to retain the contact member and the harness being adapted to be positioned by a user so that the at least one protrusion of the retained contact member contacts at least one area of the user's body on at least one side of the user's spinous process;

the pull system being connected to the contact member holder and being adapted and configured to receive a posterior-anterior (PA) force applied by the user and, when the contact member is so retained by the contact member holder and the harness is so positioned, to transmit the PA force through the contact member to the at least one area of the user's body;

the pull system comprising an elongate left strap and an elongate right strap;

the left strap having a left strap free length extending from a proximal left strap fixed end to a distal left strap free end, the left strap fixed end comprises a fixed left strap segment of the left strap that is affixed to the contact member holder;

the right strap having a right strap free length extending from a proximal right strap fixed end to a distal right strap free end, the right strap fixed end comprises a fixed right strap segment of the right strap that is affixed to the contact member holder; and the left strap being affixed to itself in a folded orientation at an upwardly inclined angle relative to the fixed left strap segment at a first left strap fold at the left strap fixed end, the right strap being affixed to itself in a folded orientation at an upwardly inclined angle relative to the fixed right strap segment at a first right strap fold at the right strap fixed end, the left strap and the right strap comprising respective first free strap segments which, in a relaxed state, extend distally from the first folds, at the upwardly inclined angles, so as to cross and form an "X" overlapping the contact member when the contact member is retained by the contact member holder, the folds tending to resist straightening of the respective first free strap segments relative to the respective fixed strap segments when the respective straps are tensioned by the PA force.

2. The back mobilizer harness of claim 1, further comprising the left and right straps comprising a second left strap fold and a second right strap fold, respectively, each second fold forming a distal end of the respective first free strap segment, the second folds forming a proximal end of a left second free strap segment and a right second free strap segment, respectively, so that, in a relaxed state of the strap, the respective second free strap segment extends generally horizontally over the contact member holder, each second fold resisting straightening of the respective second free strap segment relative to the respective first free strap segment.

3. The back mobilizer harness of claim 2, further comprising a third left strap fold and a third right strap fold, respectively, each third strap fold being upturned so as to define a distal end of the respective second free strap segment, each third strap fold further defining a proximal end of a respective third free strap segment, the third free strap segments being angled upwardly relative to the second free strap segments when the straps are in relaxed states.

* * * * *